US006870626B2

(12) United States Patent
Autrey et al.

(10) Patent No.: US 6,870,626 B2
(45) Date of Patent: Mar. 22, 2005

(54) ARRAY-BASED PHOTOACOUSTIC SPECTROSCOPY

(75) Inventors: S. Thomas Autrey, West Richland, WA (US); Gerald J. Posakony, Richland, WA (US); Yu Chen, San Diego, CA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/001,235

(22) Filed: Nov. 13, 2001

(65) Prior Publication Data

US 2003/0090663 A1 May 15, 2003

(51) Int. Cl.[7] ............................................... G01N 21/59
(52) U.S. Cl. ...................................... 356/432
(58) Field of Search ................. 356/432, 440; 73/24.02

(56) References Cited

U.S. PATENT DOCUMENTS

| | | | | | |
|---|---|---|---|---|---|
| 3,811,782 | A | * | 5/1974 | Kerr ........................... | 356/432 |
| 3,948,345 | A | * | 4/1976 | Rosencwaig .................. | 73/579 |
| 4,028,932 | A | * | 6/1977 | Rosencwaig .................. | 73/579 |

(List continued on next page.)

FOREIGN PATENT DOCUMENTS

| | | |
|---|---|---|
| DE | 10004816 | 8/2001 |
| EP | 0 142 481 | 5/1985 |
| EP | 0 369 176 | 5/1990 |
| JP | 55 010534 | 3/1980 |
| JP | 55 010535 | 3/1980 |
| WO | WO 92 21973 | 12/1992 |
| WO | WO 97 49989 | 12/1997 |
| WO | WO 98 15501 | 4/1998 |
| WO | WO 01 57498 | 8/2001 |

OTHER PUBLICATIONS

Cortese, J., "Technology Improvements are Pushing Microplate Readers into the 21st Century's High–Speed, Computerized World," *The Scientist*, pp. 24–27 (Oct. 2, 2000).

Hamadeh, H. and Afshari, C., "Gene Chips and Functional Genomics: A new Technology Will Allow Environmental Health Scientists to Track the Expression of Thousands of Genes in a Single, Fast and Easy Test," *American Scientist*, vol. 88, pp. 508–515 (Nov.–Dec. 2000).

Saeks, J., "Biochip Market Experiences Explosive Growth," *Genetic Engineering News*, vol. 21, No. 10 (May 15, 2001).

GeneMachines' OmniGrid™ Accent found at www.genemachines.com/OmniGrid/accent.html.

Packard BioScience's SpotArray Enterprise found at www.packardbioscience.com/products/products.asp?content_item_id=332.

Packard BioScience's BioChip Arrayer found at www.packardbioscience.com/products/products.asp?content_item_id=331.

Packard BioScience's SpotArray 24 found at www.packardbioscience.com/products/products.asp?content_item_id=449.

"Listen to Molecules with Pulsed–Layer Photoacoustics," found at www.qnw.com/photoacoustics.htm.

"The Gas Detection Method: Light into Sound," found at www-tracegasfac.sci.kun.nl/whatis.htm.

Packard Bioscience Company Advertisement, Science, vol. 289, Aug. 18, 2000, Circle No. 16.

Primary Examiner—Richard A. Rosenberger
(74) Attorney, Agent, or Firm—Klarquist Sparkman, LLP (57) ABSTRACT

Methods and apparatus for simultaneous or sequential, rapid analysis of multiple samples by photoacoustic spectroscopy are disclosed. A photoacoustic spectroscopy sample array including a body having at least three recesses or affinity masses connected thereto is used in conjunction with a photoacoustic spectroscopy system. At least one acoustic detector is positioned near the recesses or affinity masses for detection of acoustic waves emitted from species of interest within the recesses or affinity masses.

4 Claims, 5 Drawing Sheets

U.S. PATENT DOCUMENTS

| | | | | |
|---|---|---|---|---|
| 4,236,827 A | * | 12/1980 | Horiba et al. | 356/437 |
| 4,276,780 A | * | 7/1981 | Patel et al. | 73/643 |
| 4,436,428 A | * | 3/1984 | Watanabe et al. | 356/432 |
| 4,533,252 A | * | 8/1985 | Cahen et al. | 356/432 |
| 5,348,002 A | * | 9/1994 | Caro | 600/310 |
| 5,479,259 A | | 12/1995 | Nakata et al. | |
| 5,492,840 A | | 2/1996 | Malmqvist et al. | |
| 6,006,585 A | | 12/1999 | Forster | |
| 6,108,096 A | * | 8/2000 | Ushio et al. | 356/432 |
| 6,191,846 B1 | | 2/2001 | Opsal et al. | |
| 6,236,455 B1 | | 5/2001 | Autrey et al. | |
| 6,244,101 B1 | | 6/2001 | Autrey et al. | |
| 2002/0017617 A1 | | 2/2002 | Schuth et al. | |

* cited by examiner

ARRAY-BASED PHOTOACOUSTIC SPECTROSCOPY

This invention was made with Government support under Contract DE-AC0676RLO1830 awarded by the U.S. Department of Energy. The Government has certain rights in this invention.

FIELD OF THE INVENTION

The present invention relates to photoacoustic spectroscopic analysis and more particularly to array-based photoacoustic spectroscopic analysis.

BACKGROUND

The science industry, and the bioscience and environmental industries in particular, rely on the analysis of large numbers of samples for various studies. The need for rapid turnaround time coupled with the high costs of labor and chemical waste disposal have resulted in the development of automated array-based techniques that analyze samples using optical spectroscopy. Although these conventional absorption-based techniques are applicable to a wide spectrum of analytes, they have low sensitivity.

The two major types of optical spectroscopy currently used in array-based analysis include absorption spectroscopy and fluorescence spectroscopy. The most common technique is conventional absorption spectroscopy. Light at a given wavelength is transmitted through the sample, and the decrease in intensity relative to the original beam is monitored. The concentration of absorbing substance is determined using the Beer-Lambert law, which requires knowledge of the intrinsic absorptivity of the substance, the path length of light through the sample, and the ratio of incident and transmitted light intensities. Because direct measurement of absorption involves sensing a small decrease in the strength of a high background signal (i.e., the intensity of the unblocked light beam), conventional absorption spectroscopy is a low signal-to-noise technique. As a consequence, it has limited sensitivity (typically on the order of $10^{-3}$ absorbance units, corresponding to absorption of about 0.2% of the incident light by the sample). This analysis method does, however, have wide applicability. A large number of analytes that absorb light at sufficient concentrations can be detected efficiently by a decrease in transmissivity.

The other major type of spectroscopy in common use with sample arrays is fluorescence spectroscopy. This technique also relies on absorption of incident light by the sample, but detection is based on the emission of light of lower energy (longer wavelength) as the absorber decays from the excited state. The background signal of the detector, therefore, is zero (except for "dark current" noise in the electronic circuitry), and the signal-to-noise is very high.

The sensitivity of fluorescence depends not only on the absorptivity of the sample, but on the intensity of the incident light and the quantum yield of the conversion of absorbed energy to fluorescent light. Under optimal conditions, fluorescent samples can be measured at a sensitivity of about $10^4$ better than conventional absorbance spectroscopy. This sensitivity, however, is achieved at the cost of versatility. Few analytes fluoresce with the yield needed for wide application of the technique. Fluorescence spectroscopy is made practical for non-fluorescing analytes by tagging them with large (e.g., ca. 500 Dalton) fluorescent molecules, thus adding an additional costly step in the overall analysis and possibly altering the chemistry of the analyte in the process.

Although both conventional absorption spectroscopy and fluorescence spectroscopy rely on the absorption of light by the analyte, they differ significantly in their sensitivity and versatility. Absorption spectroscopy is easily applied to a wide variety of analytes, but has inherently poor sensitivity. Fluorescence spectroscopy is sensitive, but only for a limited number of molecules. An array-based analysis technique is needed that combines the strengths of these two spectroscopic approaches to yield both high sensitivity and wide applicability.

Photoacoustic spectroscopy (PAS) is based on the absorption of light energy by a molecule. The signal in PAS, however, is not detected by monitoring the transmittance or emission of light. Instead, in PAS, the signal is monitored by acoustic detection. Specifically, photoacoustic spectroscopy detection is based on the generation of acoustic waves as a consequence of light absorption. Absorption of light by a sample exposed thereto excites molecules in the sample to higher ro-vibrational/electronic states. Collisions of the molecules transfer the ro-vibrational energy to translational energy, i.e., heat. Modulation of the light intensity (turning the light on and off as the sample is exposed) causes the temperature of the sample to rise and fall periodically. The temperature variation of the sample is accompanied by a pressure variation that creates a sound wave (gas samples must be in a closed volume). The sound wave can be detected with a sensitive microphone.

Conventionally, a sample to be analyzed by photoacoustic spectroscopy is placed in a cuvette or other similar singular sample holder. Although obtaining the advantage of PAS analysis selectivity and sensitivity, the known singular sample analysis is slow and labor intensive. Accordingly, there is a need for PAS analysis sample apparatus and methods that allow rapid PAS analysis. Further, there is a need for sample apparatus including acoustic detectors operable with PAS apparatus and methods that allow for rapid PAS analysis.

SUMMARY

Presently disclosed are methods and apparatus for simultaneous or sequential, rapid analysis of multiple samples by photoacoustic spectroscopy (PAS). More particularly, photoacoustic spectroscopy sample arrays are disclosed. The sample arrays include a support having an array of affinity masses. The affinity masses comprise a material capable of retaining a sample having one or more analytes or capable of retaining the analyte itself, for PAS analysis. The affinity masses may comprise material having a specific affinity (chemical or physical) for the solution containing the one or more analytes of interest or for the analytes themselves. In one embodiment, the affinity masses may be formed on and/or connected to the sample array support. In another embodiment the sample array includes recesses formed in the support or formed in a substrate connected to the support. The recesses may retain affinity mass material for retaining analytes of interest. Alternatively, the recesses may simply retain solutions including one or more analytes of interest. Further, embodiments of the sample array may include at least one acoustic detector acoustically connected to or placed in the vicinity of the support to detect acoustic waves emitted by analytes of interest retained by the affinity masses of the sample array apparatus.

Also disclosed are methods for analyzing multiple analyte samples by photoacoustic spectroscopy. The multiple samples may be analyzed by PAS either sequentially or simultaneously in the sample arrays.

DETAILED DESCRIPTION

The present invention comprises photoacoustic spectroscopy sample array apparatus and photoacoustic (PAS) analysis methods using the same. Specifically, PAS sample arrays and methods of the present invention provide for rapid sequential or simultaneous PAS measurement of multiple samples in a single array, e.g., samples arranged in an n, m matrix. The present invention PAS methods and sample arrays may be used to analyze gas, liquid, and solid samples for any type of species capable of absorbing incident electromagnetic energy. For example, the sample arrays and PAS analysis methods disclosed herein may be used to speciate various organic and inorganic transition, actinide, and lanthanide metals in solution, biomass fermentation, DNA and RNA, bacteria, to monitor serum glucose levels, and to detect pH and $CO_2$, oil in water, water in oil, hydrogen gas, components of a gas headspace, non-destructive measurement of Cr(VI), and various species dissolved in a glass matrix.

Figure 1:
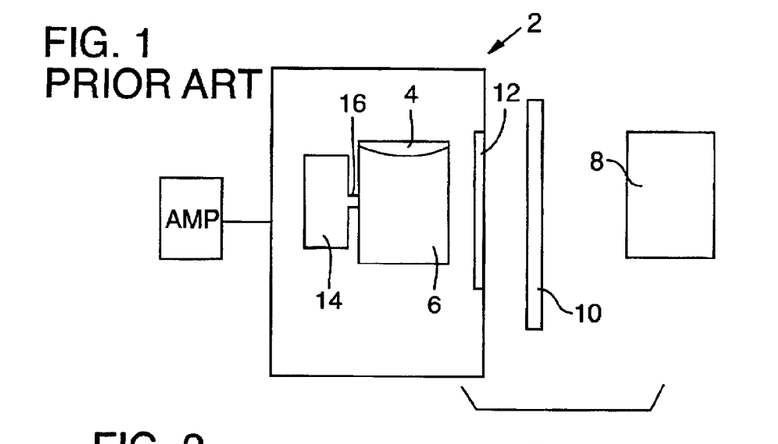
FIG. 1 shows a conventional photoacoustic spectroscopy apparatus.

With reference to FIG. 1, in a conventional PAS system 2, a single sample cuvette 4 holds a sample 6 for analysis. The sample 6 to be analyzed is irradiated intermittently by an excitation source 8, light of a selected wavelength. The excitation source 8 typically comprising a pulsed electromagnetic energy source or light is emitted from a cw source (not shown) and is optically directed to a light chopper 10, typically a slotted disk that rotates to effectively "switch" the light from the excitation source on and off. The intermittent light travels through optical filters 12 to deliver intermittent light of a selected wavelength. The light enters the cuvette 4 containing the sample 6. As the sample 6 absorbs energy from the light, an acoustic signal is generated. The acoustic signal is detected by an acoustic detector 14, typically a piezoelectric transducer or a microphone that is connected to the cuvette 4 directly or via an acoustic channel 16. An amplifier 18 is electrically connected to the acoustic detector 14 to receive and amplify electrical output from the acoustic detector 14. Such conventional PAS systems 2 may be utilized to analyze samples in the presently disclosed sample array apparatus.

The present PAS methods and sample arrays take advantage of the fact that the measurable physical parameter in PAS analysis is the acoustic signals generated by changes in pressure ($\Delta P$) due to absorption of electromagnetic energy. Thus, the unique properties of PAS absorption are amenable to minute-sized sample volume analyses. Specifically, the amplitude of the PAS signal, directly proportional to the $\Delta P$, is dependent only on the density of the absorbed energy. In other words, the signal may be represented as:

$$\text{Signal} \sim \Delta P \sim (\beta/\alpha C_p \rho)(E_{abs}/V_o)$$

wherein $\Delta P$ is the pressure change in the sample, $\beta$, $\alpha$, $C_p$, and $\rho$ are the thermoelastic properties of the solution or matrix expansivity, compressibility, heat capacity, and density, respectively, $E_{abs}$ is the quantity of energy in joules absorbed by the sample and $V_o$ is the irradiated volume (the irradiated volume is either less than or equal to the volume of the sample). As the path length is reduced both the absorbed energy and the volume are reduced simultaneously. Thus, the signal remains constant.

When the $E_{abs}/V_o$ ratio is greater than or equal to about 0.1 (Joules/liter), it is possible to measure a photoacoustic signal. For example, when an analyte is "contained" within the small volume of a sample array affinity mass or recess, the conditions are optimal for photoacoustic detection. For example, consider an array affinity mass that is 0.1 mm in diameter and 0.1 mm in height, the sample volume is $V_{affinity\ mass} = 8 \times 10^{-4}$ L ($V = \pi r^2 l$, where r=50 microns and l=100 microns) and the entire affinity mass is irradiated with an excitation source, $V_o = V_{affinity\ mass}$.

To maintain an energy density ($E_{abs}/V_o$) greater than or equal to about 0.1 (assuming $V_o = 8 \times 10^{-4}$ μL is the irradiated volume on the micorarray) the sample or analyte must absorb $E_{abs}$ ca. $8 \times 10^{-5}$ μjoules of the incident energy. The amount of energy absorbed by the analyte depends on both the absorbance (A) of the sample and the quantity of incident energy ($E_{incident}$).

$$E_{abs} = E_{incident}(1 - 10^{-A})$$

For a sample with an absorbance of 1 ($cm^{-1}$) the amount of light absorbed across the 0.1 mm thick affinity mass is relatively small, ca. 0.002%. Rearrangement of the above equation determines the required incident energy necessary to observe a photoacoustic signal as follows:

$$E_{incident} = E_{abs}/(1 - 10^{-A})$$

$E_{incident}$ ca. 5 μjoules, for an affinity mass of about 0.1 mm in diameter and 0.1 mm in height and a sample with an absorbance of 1 $cm^{-1}$ measured in a conventional PAS spectrometer.

Even if the microarray affinity mass is larger (e.g., >0.1 mm diameter), if the excitation source is "collimated" to a diameter of about 100 microns, the same assertions set forth above hold true because the photoacoustic signal is proportional to the excitation volume, not the path length.

As based on the above, for a given concentration of molecules, e.g., dissolved in a solution, absorbed into or onto an affinity mass or bound to a DNA or RNA-type chip, differing sample volumes will provide the same measurable signal. Thus, sample volume can be decreased significantly without a loss in sensitivity.

Furthermore, because $\Delta P$ is a measure of the force per unit area, the signal is independent of the size of the detector (the detector having sufficient electrical capacitance and an area less than or equal to the area of the cross sectional excited volume). Accordingly, the present invention provides for a reduction in both the sample volume and the acoustic detector area, allowing rapid, array-based PAS sample analyses without a loss in analytical selectivity or sensitivity. The present invention provides not only PAS methods for simultaneous or sequential multiple sample array PAS analyses and sample array apparatus but also provides as much as a thousand fold increase in detection sensitivity as compared to conventional, single sample cuvettes, without sacrifice as to analyte applicability.

PAS Sample Arrays

Figure 2:
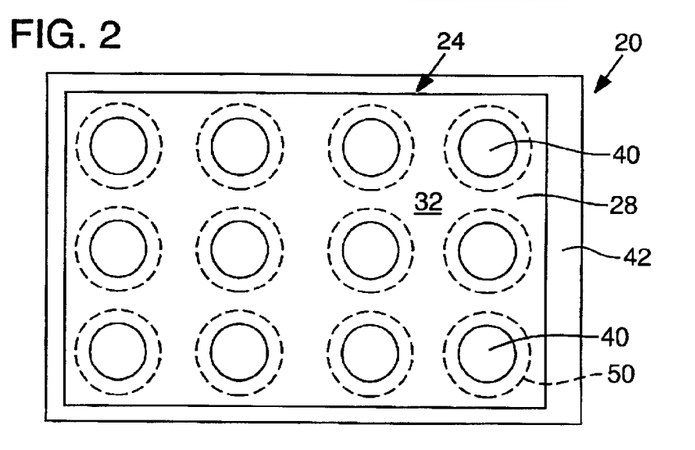
FIG. 2 is a top view of an embodiment of a sample array including an acoustic detector positioned at each affinity mass.
Figure 3:
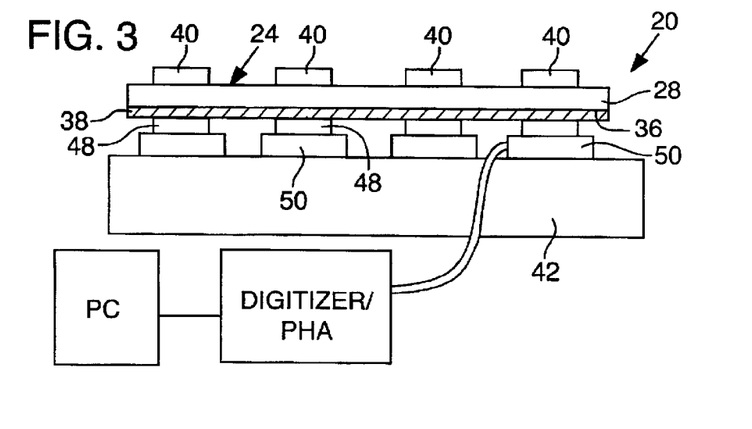
FIG. 3 is a side view of the sample array illustrated in FIG. 2.

FIG. 2 is a top view of an embodiment of a sample array apparatus 20. This embodiment of the sample array 20 comprises a body 24 preferably including a support 28 with an upper surface 32 and a lower surface 36 (FIGS. 2 and 3). Body 24 may further comprise a reflective coat or plate 38 (FIG. 3) connected to the upper or lower surface of the support 28. Body 24 further includes multiple affinity masses 40 formed on or connected to the support 28 to form an arrangement or array of sample containers, e.g., an n, m matrix as shown in FIG. 2. The sample array 20 may further include one or more acoustic detectors 48 (FIG. 3) electrically connected via suitable electronic circuitry 50 (integrated circuitry for relatively small acoustic detectors, as discussed below) to a digitizer/photoacoustic amplifier that converts the acoustic detector signal to a digital signal. A PC may be used to analyze the digital signal from the digitizer/amplifier. The digitizer/photoacoustic amplifier and the PC are typically part of the PAS system used to analyze samples in a sample array of the present invention. The sample array 20 may further include a base plate 42 that is formed of any rigid material sufficient to support the body 24, and the one or more acoustic detectors 48 and corresponding electronic circuitry 50.

The support 28 is formed of any sufficiently rigid material upon which affinity masses 40 may be connected and adequately supported. The support 28 material preferably does not significantly impede transfer of an acoustic signal from an analyte in the affinity mass 40 to an acoustic detector 48. That is, the material forming support 28 preferably has sufficient sound transmission properties for PAS analysis (as known to those persons skilled in the art). For example, the support 28 may comprise a glass such as PYREX, borosilicate, quartz (e.g., a conventional microscope slide). Alternatively, the support 28 may comprise a polymer substrate, such as polystyrene, LUCITE or TEFLON.

The affinity mass 40 is preferably a solid material or sufficiently viscous liquid such that it maintains its shape when placed on or formed on the support 28. (The affinity mass may comprise a liquid or gas and be placed in recesses in the support as described below in relation to other sample array embodiments.) Although illustrated in FIGS. 2 and 3 as cylindrical in shape, the affinity masses may take any shape or form capable of being irradiated, e.g., cylindrical or half spheres (droplets). For example, the affinity masses 40 may be cubic-shaped matrixes 1 mm wide by 1 mm deep by 100 microns high. The affinity masses 40 may be relatively small, e.g., 50 micron by 50 micron by 1 micron in height (but a preamplifier would preferably be placed at each acoustic detector for affinity masses of such size). The affinity mass 40 is preferably of a shape that maximizes an acoustic to electric energy transfer at the acoustic detector 48 (FIG. 3). For example, if the acoustic detector 48 comprises a transducer forming a flat surface, an affinity mass in the form of a substantially flat lower surface, as shown in FIGS. 2 and 3, provides good sensitivity.

Affinity masses may be of exceptionally small volume as low as nanoliter or picoliter ranges (or lower if a suitable acoustic detector is used). Affinity masses 40 may even be of sufficiently small volumes so as to retain a few or even a single molecule of a species of interest. The molecule or molecules of the species of interest adhere to the affinity mass by chemical or physical attraction of the species for the affinity mass material, such as by hydrogen bonding, ionic interactions, size exclusion, partitioning by solubility, etc.

The affinity masses 40 are formed of any material having a sufficient affinity (chemical or physical) for the species of interest, e.g., nucleic acids (such as DNA and RNA), proteins, an organic compound, an enzyme, an inorganic metal such as chromate, so as to retain the species in the affinity mass. Thus, the affinity mass material is chosen depending upon the species of interest (as known to those persons skilled in the art). For example, the material forming affinity mass 40 may comprise an organic film having an affinity for an organic vapor species of interest, wherein the organic species of interest partition into the affinity mass because the species are soluble in the organic film forming the affinity mass. Further examples of possible affinity mass materials may comprise a cationic material having an affinity for an anion analyte of interest, or a self-assembled monolayer (e.g., long chain aliphatic compounds, e.g., $C_{10}-C_{20}$) a with a head group (including, e.g., functionalized groups, such as carboxylic acid to make the surface of the substrate attractive to molecules that interact with the carboxylic group, for example an organic amine or a metal cation) that has an affinity for an organic amine or acid of interest. Another example of possible affinity mass 40 material may is polyethylene that may be applied as a film for attracting and retaining toluene in a gas sample for PAS analysis. The quantity of toluene in the gaseous sample could then be determined based on PAS analysis by determining the amount of toluene in the affinity mass and utilizing the partition coefficient of toluene in polyethylene.

The affinity masses 40 may be formed by use of for example microarray fabrication technologies. As known to those persons skilled in the art, plates or substrates may be derivatized using conventional equipment (e.g., as made by GeneMachines (the OMNIGRID arrayer) or Packard Bio-Science (such as the SPOT ARRAY or the BIOCHIP arrayers) to make such affinity masses in "microarrays." Certain commercially available ready assembled arrays, such as DNA and RNA chips may be used for a sample array by PAS (for DNA/RNA analysis in this specific example) (see, e.g., Gene Chips and Functional Genomics, *American Scientist*, 8, pp. 515 and Well Read, *The Scientist*, Oct. 2, 2000, pp. 24–27, which are incorporated herein by reference). Alternatively, a support may be formed of materials discussed above and affinity masses may be formed thereon in various manners as would be known to those persons skilled in the art. For example, affinity masses may be formed on a substrate (such as a polymer substrate) by spin coating (or other suitable deposition method) a thin film of material having the desired affinity, and then masking and etching the thin film to form the affinity masses. The thin film is masked and etched in a manner to leave affinity masses of desired shapes, dimensions, and locations on the substrate.

A reflective coat or plate 38 may be connected to or formed on the upper surface 32 or lower surface 36 of the support 28. The reflective coat or plate 38 comprises any material capable of reflecting the irradiation directed from a radiation source in a PAS system into samples retained within the affinity masses 40, without significantly impeding the transfer of an acoustic signal from the affinity masses 40 to one or more acoustic detectors 48. For example, the reflective coating or plate 38 may comprise a metal, such as aluminum, gold, or may comprise a mirror.

Figure 5:
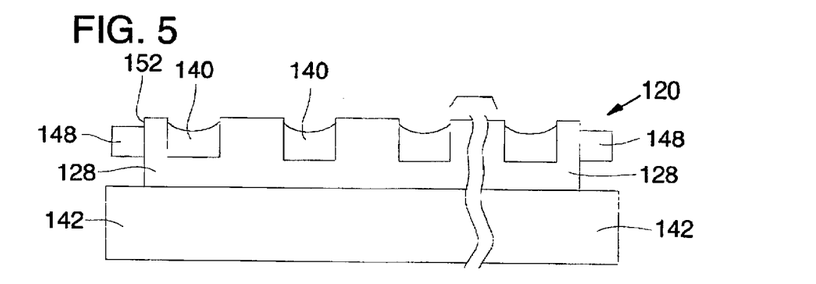
FIG. 5 is a side view of an embodiment of a sample array including one or more side-mount acoustic detectors.
Figure 6:
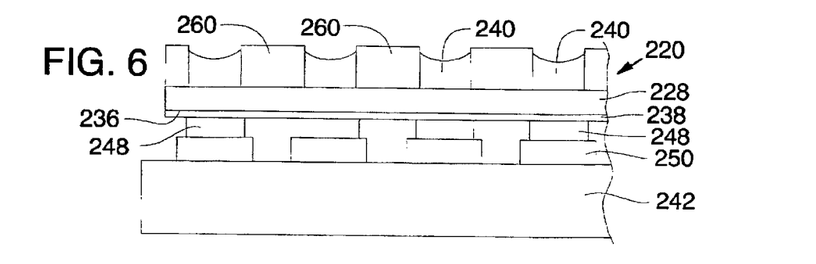
FIG. 6 is a side view of an embodiment of a sample array including an acoustic detector positioned at each sample container.

As shown in FIGS. 5 and 6, alternative embodiments of the sample array apparatus include sample containers comprising recesses formed in (or connected to) the support. Such recesses may hold the sample to be analyzed or may contain affinity masses that are not sufficiently viscous to form their own entity on the support (or as a way to pre-define the shape of the affinity mass (viscous or nonviscous)). For example, FIG. 5 illustrates a transmissive sample array apparatus 120 including recesses 140 formed in or connected to a support 128. The recesses 140 may be of any shape and size suitable for PAS analysis, as is known by those persons skilled in the art. The recesses may be of relatively small volumes (as discussed above relative to affinity masses). Small volume recesses may be formed by known photolithographic techniques, such as by masking and etching to form recesses 140 in the same material that forms the support 128. Alternatively, material may be photolithographically formed on the support to form recesses 140.

The embodiment shown in FIG. 5 may further include a base plate 142 to carry the support 128 if the support is not sufficiently rigid to support the recesses. One or more acoustic detectors 148 may be formed on or connected to the sample array 120, such as mounting on the base plate 142 such that the detectors are aligned beneath the recesses 140 (as shown in FIG. 6) or side-mounted to the support 128 (shown in FIG. 5).

As shown in FIG. 6, another embodiment of a sample array 220 includes a body 224 comprising a support 228 with an upper surface 232 and a lower surface 236. Body 224 may further comprise a reflective coat or plate 238 connected to the support 228. Body 224 further includes multiple recesses 240 formed in the support 228. Alternatively, the recesses 240 may be formed in or by a substrate 260 that is connected to the support 228. (As with other embodiments of the sample array apparatus, the recesses may retain an actual sample to be analyzed or may retain an affinity mass that will in turn retain the sample or species to be analyzed.)

The sample array 220 may further include one or more acoustic detectors 248 electronically connected via suitable electronic circuitry 250 to a digitizer/photoacoustic amplifier (not shown) that converts the acoustic detector signal to a digital signal (integrated circuitry for such connection may be necessary for relatively small detectors as discussed below). A PC (not shown) may be used to analyze the digital signal from the digitizer/amplifier. The sample array 220 may further include a base plate 242 that is formed of any material sufficient to support the body 224, the one more acoustic detectors 248, and the electronic circuitry 250.

Although the sample array apparatus shown in FIG. 5 (and other embodiments) comprises a transmissive sample array with one or more side-mount detectors and the sample array apparatus shown in FIG. 6 comprises a reflective array with one or more bottom-mount acoustic detectors, it is to be understood that acoustic detectors on such apparatus may be placed in a variety of locations on the array or may be a part of the PAS system wherein the sample arrays of the invention are aligned such that the acoustic detectors can detect signals from the recesses.

Figure 12A:
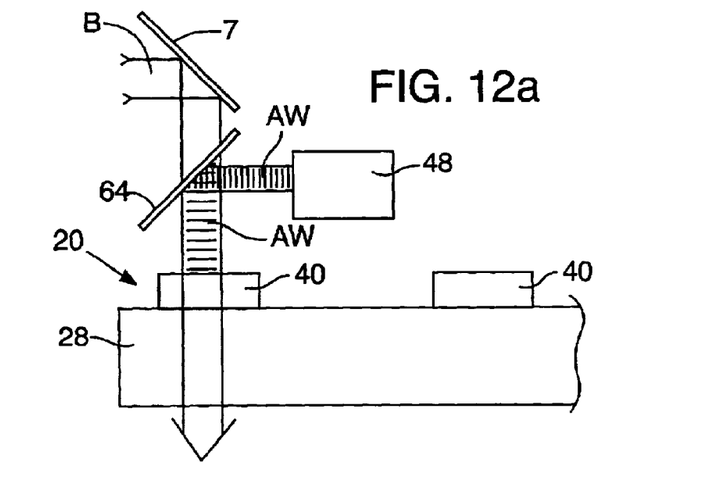
FIG. 12a shows an embodiment of a sample array for use with a PAS system having air-coupled acoustic detection.
Figure 12B:
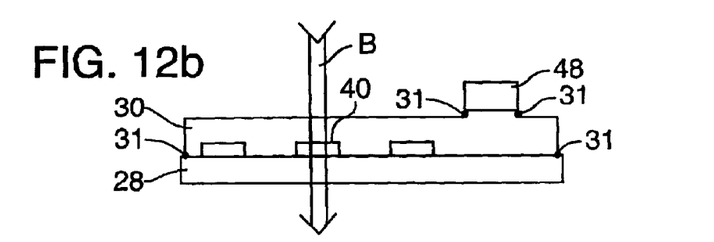
FIG. 12b shows an embodiment of a sample array for use with a PAS system having air-coupled acoustic detection and a sealing cap.

Sample arrays including recesses (e.g., 140, 240 as shown in FIGS. 5 and 6, respectively) may additionally include a sealing plate that effectively seals all of the sample recesses after samples have been deposited into the recesses (or into affinity material in the recess). For example, as shown in FIG. 12b, a sealing cap 30 comprised of a material transmissive to the desired incident light beam B. The sealing cap 30 preferably includes any suitable means 31 to ensure a substantially airtight seal between the support 28 and the cap 30 and between the cap 30 and an air-coupled acoustic detector 48. For example, rubber gaskets or seals formed of materials such as TEFLON, KALREZ, copper, VITON, and epoxy may be used. With such a sample array, there is no need to include a reflective layer or plate because the acoustic detector 48 is air-coupled to the sealed sample array at a location outside of the path of the light beam B. With such a sample array, as the sample is heated, the total gas volume in the recess expands against the detector providing increased sensitivity. If the sealed sample array were to be further filled or compressed with a gas, e.g., helium, the sensitivity may be further increased.

Figure 7:
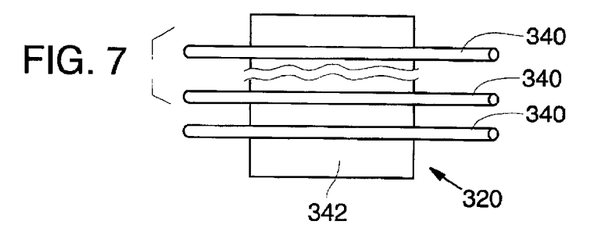
FIG. 7 is a top view of another embodiment of a sample array, wherein the analyte containers comprise capillaries.
Figure 8:
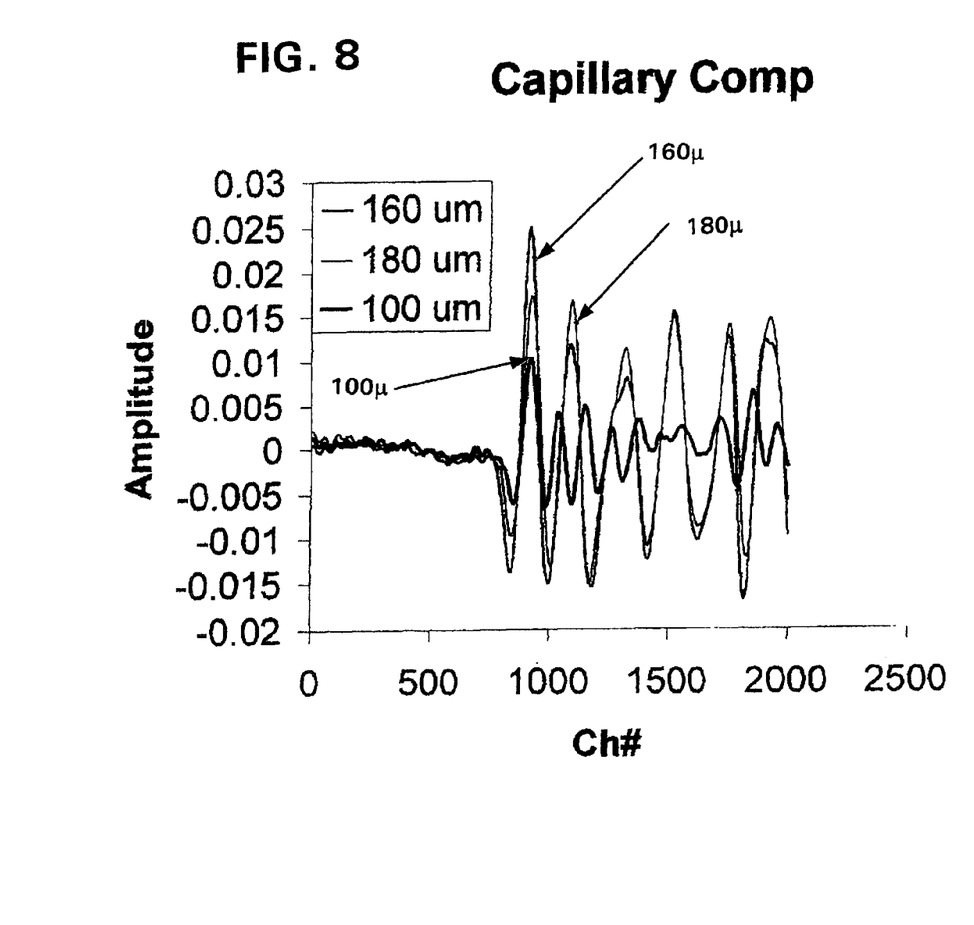
FIG. 8 is a graph of PAS signal amplitude for various capillaries of a reflective-type sample array similar to the sample array shown in FIG. 7.

As shown in FIG. 7, in yet another alternative embodiment of the sample array apparatus 320, the apparatus includes sample containers comprising multiple capillary tubes 340. Such a sample array 320 may include three or more capillaries 340 for retaining samples containing species of interest, or for retaining affinity masses that in turn retain species of interest. For example, microbore capillary tubing may be used to form the multiple sample containers of the sample array 320. Capillaries 340 may be formed of any material transparent to the light source for example fused-silica or a TEFLON co-polymer (such as PEEK) for use with e.g., a mid-IR light source system. Capillaries 340 may have a variety of diameters. Good results have been obtained with capillaries having diameters of from about 100 $\mu$M to about 180 $\mu$M (see FIG. 8) but larger or smaller diameter capillaries may be used. Such capillaries 340 may be sealed with suitable high-pressure fittings so that gaseous samples may be analyzed or to analyze samples under increased pressure (e.g., up to about 60,000 PSI), as shown in U.S. patent application Ser. No. 09/766,251.

Sample array 320 preferably further includes a base plate 342 for supporting the capillaries 340. As with other embodiments of the sample array apparatus, sample array 320 may further comprise one or more acoustic detectors (not shown in FIG. 7) placed at any of a variety of locations relative to the capillaries 340, similar to the embodiments set forth above and as would be known to those persons skilled in the art. Alternatively, the sample array 320 may be used in a PAS system equipped with one or more acoustic detectors.

Figure 9:
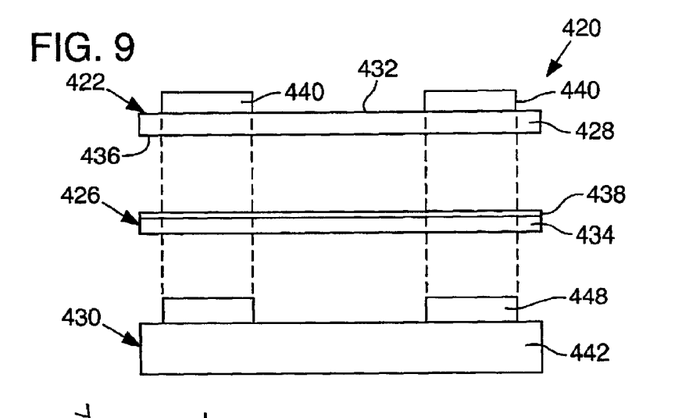
FIG. 9 illustrates the path of light waves and path acoustic waves in an embodiment of the sample array (showing a portion of the sample array embodiment).

In another embodiment, a sample array 420 may be formed of separate parts or sub-assemblies, e.g., as shown in FIG. 9. A first subassembly (or microarray plate) 422 may comprise a support 428, and affinity masses 440 formed on or connected to an upper surface 432 of the support. Alternatively, the first sub-assembly 422 may comprise a support 428 having recesses formed therein or connected thereto (similar to those of FIGS. 5 and 6). The recesses, as with the other embodiments, may either contain affinity mass material to retain a sample or may retain the just the sample to be analyzed for the species of interest. The support 428 materials (as with all embodiments of the sample array) may be the same as or similar to the supports of other embodiments discussed above.

A second subassembly (or reflective plate) 426 of the sample array 420 may comprise a reflective coating or plate 438 and a reflective-coat base 434. Alternatively, a sufficiently rigid reflective plate may be used without a reflective-coat base 434. As with other embodiments of the sample array including a reflective plate, the reflective coat or plate 438 may comprise the same or similar materials as discussed above relative to the embodiment of FIGS. 2 and 3. The second subassembly 426 may be left out of the sample array 420 assembly if the sample array is to be used as a transmissive array or if the light beam is directed to a sample at an incident angle resulting in total internal reflection (as discussed above). Alternatively, the second subassembly may be unnecessary if a reflective coat or plate is formed on or connected to a surface of the support of the first subassembly 422.

A third subassembly (or base plate) 430 of the sample array 420 may comprise one or more acoustic detectors 448 to be positioned under the affinity masses 440 (or recesses) when the subassemblies 422, 426, 430 are aligned one atop the other. The one or more acoustic detectors 448 may be formed on or connected to a base plate 442. The base plate 442 may comprise any sufficiently rigid material for supporting the acoustic detectors 448 and the first and second subassemblies 422, 426 when aligned one atop one another. Alternatively, the third subassembly 430 may comprise only a base plate 442 and acoustic detectors on a PAS system may be used to detect acoustic waves emitted from the affinity masses 440 or recesses of the sample array 420. In yet another alternative, the first sub-assembly 422 may be used without the second and third subassemblies 426, 430, and may simply be placed in a PAS system equipped with one or more acoustic detectors or equipped with a "permanent" base plate having acoustic detectors connected thereto.

Arrangement of the sample containers (such as the affinity masses 40) of the various sample array embodiments may take a variety of forms. For example, a sample array may have recesses and/or affinity masses arranged in an n, m matrix, wherein n and m are integers from 2 to as large as can be reasonably handled by operators and PAS apparatus. There may be as many affinity masses (or other form of sample container) as the body of the array can support and acoustic detectors can measure. (The sample array may be of a size and shape that is operable with conventional PAS equipment.) If in a matrix arrangement, it is understood, that either n or m of the matrix may be increased to a value greater than those shown in the figures, depending upon sample array size and detector size and arrangement (discussed below). As another example, the sample arrays may include sample containers (such as affinity masses or recesses) arranged in a stacked manner such that the sample containers are stacked or aligned one on top of another. Alternatively, multiple sample array bodies may be stacked or aligned one upon another such that sample containers on each body align with the sample containers on other sample array bodies in the stack.

The embodiment of the sample array 20 shown in FIG. 2, as well as alternative embodiments, may include a single or multiple acoustic detectors in a variety of locations on the sample array. For example, as shown in the embodiment of the sample array 20 illustrated in FIG. 3, an acoustic detector 48 is positioned under each affinity mass 40. The acoustic detectors 48 may comprise any suitable acoustic detector, such as microphones or transducers (e.g., piezoelectric transducers).

Embodiments utilizing arrays of acoustic detectors may require use of relatively small transducers. (Acoustic detectors may be referred to herein as "transducers" but it is to be understood that any other suitable acoustic detectors may be utilized rather than transducers.) The transducer, however, must have sufficient capacitance, which decreases with the contact area of the transducer. The transducer preferably has a cross-sectional area that is less than or equal to the cross-sectional area of the irradiated volume. Transducers having diameters as small as about 1 mm have been found to have sufficient capacitance for PAS analysis. Low transducer capacitance means low ability to drive a signal through circuitry connecting the transducer to an amplifier. To maximize voltage from a transducer, contribution to $C_{circuit}$ (associated with cables and connectors of the electronic circuitry 50) should be minimized. This may be addressed by using relatively short cables (or by placing amplifier circuitry directly on the transducer as discussed below).

For transducers smaller than about 1 mm in diameter, an amplifier circuitry formed on and used with the transducer overcomes lower capacitance of the transducer. Such a transducer/amplifier may comprise a transducer formed on a FET preamplifier (such as a MOSFET in die and wafer form available from Supertex Inc.) or a charge sensitive preamplifier in close proximity (minimized cable length) may be used when the capacitance of the piezoelectric element (a type of transducer useful in the present invention) is too small to use conventional coax cable. Several commercial sources (e.g., Kistler, Panametrics, Pateq and PCB) supply integral electronic signal conditioning (preamplifiers) built into the piezoelectric element or transducer.

To determine when preamplification (i.e., integrated circuitry or integral electronics including an amplifier on the transducer) is preferred for any particular transducer material, thickness, or diameter, the following guidelines may be used. In general, when capacitance is not an issue (for piezoelectric transducers with diameters greater than 5 mm) use of a resonant frequency $f_{tr}$ that is optimized for the acoustic time constant ($\tau_r$) may be used. Transducers measure the transient pressure change as a consequence of heat deposited into solution as a function of time. If the heat is deposited over a time period that is long compared to the time constant of the resonant transducer ($\tau_{tr}=1\ f_{tr}$) the observed voltage response will be attenuated. Preferably, the ratio of ($\tau_{tr}$)/($\tau_r$)~1, and is greater than one. The acoustic time constant ($\tau_r$) is dependent on the pulse width ($\tau_p$) of the excitation source and the acoustic transient time ($\tau_a$) across the excited volume $V_o$ as follows:

$$\tau_r = (\tau_a^2 + \tau_p^2)^{1/2}$$

The acoustic transient time is the time it takes for the acoustic wave to travel across the excitation volume ($\tau_a$)= $d/v_s$ where d is the diameter of the irradiated volume ($V_o$) and $V_s$ is the speed of sound in the matrix. For a sample depth of about 100 microns, $\tau_a$ is ca. 50 ns assuming $V_s$~2 mm/μs for a viscous fluid matrix. To calculate optimum piezoelectric frequency ($f_{tr}$) choices for photoacoustic detection, two cases for $\tau_{p1}$ long excitation pules ($\tau_p > \tau_a$) and short excitation pulses ($\tau_p < \tau_a$) are considered. For short pulse excitation, $\tau_r \sim \tau_{a1}$, $f_{tr}$<20 MHz is preferable and for long pulse ($\tau_p$=0.5 µs) excitation, $\tau_r \sim \tau_{p1} f_{tr}$<2 MHz is preferable. Given this comparison, the low frequency transducer may appear best to detect PA signals from either short or long pulses. In addition, the voltage output from a transducer is directly proportional to the thickness (h) of the piezoelectric element. (A 2 MHz piezoelectric element is 10 times thicker than a 20 MHz piezoelectric element of the same material and to a first approximation gives a signal an order of magnitude larger for the same transient pressure wave.) The static capacitance of the piezoelectric transducer, however, is inversely proportional to the element thickness (h) as follows:

$$C_o = (1/h)(\pi d^2//4) K^T \epsilon_o$$

where $K^T$ is the dielectric constant of the material and $\epsilon_o$ is the permeability of space ($\epsilon_o$=8.85 pF/m) and d is the diameter of the element (d).

Thus, as the diameter of the piezoelectric element is reduced the capacitance of the transducer decreases rapidly. To compensate for the decrease in transducer diameter, the thickness of the transducer may be decreased (forcing a higher frequency use over lower frequency). Therefore, preferably, the transducer is formed of a piezoelectric material having relatively large dielectric properties, e.g., PZT 5H, $K^T$=3400. For the above two conditions, i.e., long and short excitation pulse, static capacitance of the transducer can be calculated from the equation above, for a 20 MHz PZT 5H piezoelectric $C_o$=250 pF and for a 2 MHz PZT 5H piezoelectric $C_o$=25 pF for a 1 mm diameter PZT 5H element. The capacitance of conventional cable used to connect transducer to preamplifiers is ca. 30 pF/ft. Thus, with a higher frequency transducer there are no capacitance concerns. For low frequency transducers, however, the cable length must be minimized.

Thus, for a PZT 5H transducer, integral electronics is preferable when the diameter of the PZT 5H transducer is decreased to values less than about 1 mm in diameter and/or at frequencies less than about 2 MHz.

Figure 13:
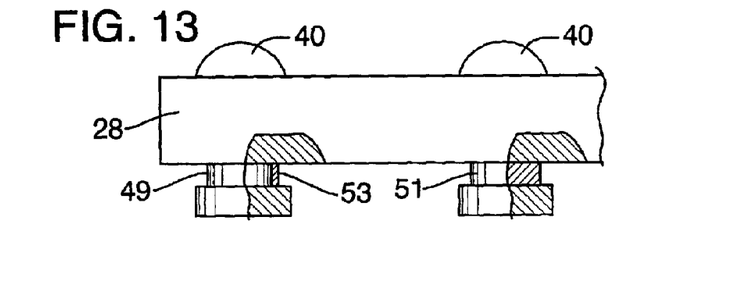
FIG. 13 is a side view of an embodiment of a sample array including a piezoelectric tube transducer.

Alternatively, piezoelectric thin-wall tube transducers 49 (as shown on left in FIG. 13 rather than disk-type transducers 50 as shown on right in FIG. 13) may be used as small diameter acoustic detectors to provide lower frequency response and greater static capacitance than conventional piezoelectric disk detectors. With thin-wall tube transducers 49 the static capacitance is dependent on the tube 53 wall thickness as follows:

$$C_o = (2\pi K^T \epsilon_o l)/ln(d_o/d_i)$$

Wherein l and $d_o$ and $d_i$ are the length, and outer and inner diameters of the tube, respectively. For a piezoelectric thin-wall tube transducer of about 2 mm long and having a $d_o$ equal to about 1 mm, and a $d_i$ equal to about 0.8 mm, the static capacitance is about ca. 850 pF. For such an embodiment, the thin-wall transducer would not require integral electronics. As shown in FIG. 13, a thin-wall transducer 49 may be placed, for example, beneath the affinity mass 40 (e.g., beneath support 28) such that the tube 53 is substantially perpendicular to a lower surface of the support 28. Placement of a thin-wall transducer 49 may be the same as the various embodiments discussed below in relation to acoustic detectors in general.

Of the embodiments of the sample arrays that include one or more acoustic detectors, the acoustic detectors may be connected to or arranged relative to the sample containers, such as affinity masses 40 (FIGS. 2 and 3), recesses 140, 240 (FIGS. 5 and 6), and capillaries 340 (FIG. 7), using any of a variety of acoustic bridges. The detectors may be positioned to receive acoustic signals from the sample affinity masses, recesses or capillaries by direct contact (e.g., contact transducers), air coupling (e.g., air-coupled transducers) or by immersion (e.g., immersion transducers) (FIGS. 4a–4c).

Figure 4A:
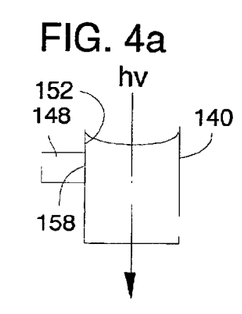
FIGS. 4a–4c show alternative acoustic bridge arrangements for embodiments of sample arrays that include one or more acoustic detectors.
Figure 4B:
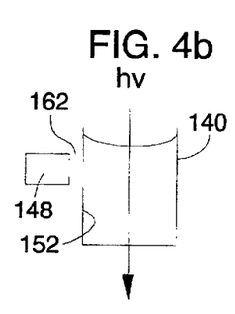
Figure 4C:
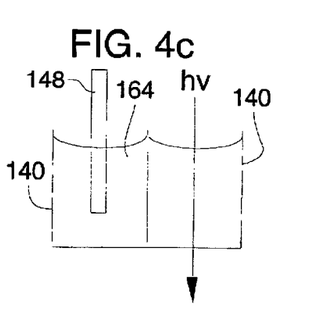

With reference to FIG. 4a, an acoustic bridge between each sample container 140 and an associated detector 148 may comprise a contact bridge 158. The contact bridge 158 is "positioned" between a wall 152 of the sample container 140 and the detector 148. An acoustic coupling fluid (e.g., grease, water, epoxy) may be placed at the contact bridge 158 between the detector 148 and an outer surface of the wall 152 of the sample container 140.

With a contact-detector type arrangement with a transmissive sample array having one or more side-mounted detectors (such as the sample array embodiment of FIG. 5) a transducer 148 is preferably in direct physical contact with a wall 152 of at least one of the recesses 140. A contact-detector arrangement as shown in the sample array embodiments of FIGS. 2, 3, and 6, may utilize a transducer 48, 248 in contact with a lower surface 36, 236 of the support 28, 228 (or a surface of a reflective coating or plate 38, 238) beneath the affinity mass 40 or may be connected directly to a bottom surface of a recess 240 to be analyzed.

Preferably, a contact transducer has significant acoustic contact with the affinity mass, e.g., a transducer may partially encapsulate a portion of the support nearest the affinity mass or recess (e.g., the wall of a sample container or lower surface of the support). A contact-detector may comprise a ceramic transducer shaped to fit against or about at least a portion of the support or the outside of the wall of a recess. If a recess or other sample support forms a curved surface, a curved contact transducer may be used. Hollow-type ceramic transducers may be filled with a flexible, acoustically transmissive material such as epoxy to minimize mechanical stress on the transducer.

Suitable ceramic-type contact transducers are available from a number of manufacturers such as PAC, Material Systems Inc., Panametrics, PCB, Stavely, or KKB. Additionally, piezoelectric crystals available from manufactures such as Channel Industries, Sensor Technology Ltd. and Valpey Fisher may be used. Piezoelectric transducers having resonant frequencies of from about 100 KHz to about 5 MHz have been found to be useful. For sample arrays including affinity masses or recesses having volumes less than about ca. 10 nL, transducers having higher frequencies, e.g., 5–100 MHZ are preferable for capacitance concerns if pre-amplifying integrated circuitry are not used. The contact detectors used may comprise flexible polymeric transducers, such as polyvinylidenefluoride (PVDF) available from Ktech (or a film transducer available from Rhone-Poulenc may be used). Flexible transducers may better accommodate slight stress differences arising from sample recess or support geometries.

Although many embodiments of the sample arrays are discussed and illustrated utilizing contact transducers, it is understood that any of the embodiments of the sample arrays including detectors, may include any suitable acoustic detector. Further, it is understood that such detectors may be arranged near or connected to the affinity masses or recesses of the sample arrays in any variety of suitable acoustic signal receiving manners (including but not limited to air-coupling and immersion coupling).

For example, in another embodiment of the sample array apparatus, the sample array may include an air-coupling acoustic bridge, wherein the acoustic bridge comprises air between an outer wall or lower surface of a recess (as shown in FIG. 4b) (or between a support for an affinity mass formed thereon) and an associated detector. In the embodiment shown in FIG. 12a (as well as the embodiment shown in FIG. 12b), a transducer 48 positioned above the sample array, is air-coupled via an air-channel 62 formed by a reflected acoustic wave emitted from illuminated affinity masses 40 of the sample array 20. A PAS system having a radiation source (incident light) emits a light beam B that is reflected by a light reflector 7 to a selected affinity mass 40 of the sample array 20. The irradiated affinity mass 40 emits an acoustic wave AW that is reflected by an acoustic reflector 64 of the PAS system to a detector 48 either fixed to or movable within the PAS system.

With air-coupled detection, the impedance boundary losses between the sample solution and the air, and between the air and the transducer may be relatively large. These losses in transmission efficiency may be mitigated by, e.g., use of a sealed affinity mass or recess (discussed above in relation to the embodiment illustrated in FIG. 12b). Air-coupled detection may be improved by utilizing a PAS system having an acoustic reflector formed of a material, such as quartz, that will transmit the light beam B but reflect the acoustic waves. Quartz transmits ca. 92% of the incident light and reflects ca. >99% of the emitted acoustic wave.

In addition to the arrangement of air-coupled detectors discussed above, the placement of detectors in the air-coupled embodiments may be essentially the same as discussed below relative to the contact transducer placements. For example, an air-coupled detector may be fixed at each recess or affinity mass 40, there may be a single or a few air-coupled detectors fixed at the end of a row or rows of sample containers or a detector may be fixed to a PAS system in which the sample array will be analyzed.

In yet another embodiment (FIG. 4c), the sample array 120 may include a detector 148 having a liquid-coupling acoustic bridge, wherein the detector 148 is immersed in a liquid in a sample recess (or affinity mass) adjacent a recess 140 to be analyzed. Such an immersion detector preferably comprises a thin probe, such as a VP-A50 probe available from Valpey Fisher, of a suitable size to fit within the affinity mass or recess volumes of the sample array. The immersion detector would likely be a part of a PAS system and may be fixed to the PAS system (and the sample array moved) or may be movable within the PAS system such that it can be moved and placed in an affinity mass or recess 140 immediately adjacent the affinity mass or recess to be analyzed. At least affinity mass or recess in the sample array would be sacrificed for the initial measurement of a first affinity mass or recess of the sample array. Thereafter, the immersion detector 148 would be moved and immersed in the affinity mass or recess 40 just previously measured for analysis of the next, immediately adjacent affinity mass or recess 40.

The sample array may include an immersion detector wherein one affinity mass or recess per row of affinity masses or recesses is sacrificed and the immersion detector is fixed in the first affinity mass or recess of the row for detecting signals from each affinity mass or recess in the row. Alternatively, a single immersion detector may be positioned in an affinity mass or recess centrally located within the sample array. Such a sample array provides a mechanically simple device as compared to a sample array requiring a PAS system having a movable detector.

Another type of immersion detector that may be used with the sample array may comprise an immersion transducer formed to fit within the recess to fit near or to contact interior walls of the recess. For example, for a sample array having cylindrically shaped recesses, the detector may be a hollow cylinder formed of a material such as PVDF or a ceramic piezoelectric that is insertable in the cylindrically recess. Further, the use of the sample fluid or affinity mass material within the recess minimizes friction during transducer placement.

Preferably, an acoustic detector would be placed at each affinity mass or recess to detect the acoustic waves generated by absorption of the incident light by the analyte bound within the affinity mass or recess (e.g., with ten affinity masses in an array, ten transducers would be used). As discussed above, the area of each individual transducer would preferably be less than or equal to the cross section area of the affinity mass or recess in the array. For example, the signal from a 100 micron diameter, (can vary in size but good results are achieved when the size is matched to the cross section of the "activated" affinity mass or recess) 5 MHz transducer (can be varied between 50 KHz to 50 GHz and made of any suitable material for a piezoelectric transducer, e.g., pzt or quartz) is attached to the bottom of a support directly below the affinity mass or recess. Electronic integrated circuitry (IC) may be used to capture and amplify the electronic signal from the transducer. Leads from transducer electrodes (preferably gold plated but the electrodes may comprise other conductive material, e.g., silver, platinum) are attached to a FET preamplifier. Gold electrodes can act as a reflective surface to reflect the incident excitation energy back through the matrix microarray. Alternatively, the reflective coating or plate discussed above, e.g., a dielectric coating or a silver, gold or aluminum mirror is incorporated between the transducer and the support to reflect the incident light. Low impedance signal output from a FET preamplifier is fed through a cable to a digitizer of a pulse-height-analyzer (PHA) to provide a measure of the photoacoustic signal magnitude. An FET (field effect transistor) takes the high input impedance signal from the transducer and converts it to a low impedance output signal that can be transferred through conventional cable to signal capture electronics (e.g., the digitizer or PHA).

When a transducer is positioned beneath each affinity mass or recess on the sample array, all of the affinity masses or recesses in the array may be irradiated and analyzed simultaneously for PAS rapid analysis. Alternatively, the affinity masses or recesses on the array may be analyzed sequentially, individually or by rows.

PAS Analyses Methods

With conventional PAS sample analysis, the light source is typically modulated and monochromatized prior to reaching the sample. Mechanically chopping the light beam from a continuous source or using a pulsed source may provide modulation. For broadband sources, use of notch filters or reflectors achieves monochromatization. For bright sources of highly absorbing samples, grating monochromators may be used. The amplitude modulation needed for PAS is obtained either by scanning continuously at an optimal mirror speed or in a step-scanning mode by dithering a mirror in an interferometer during data collection.

Conventional light sources for PAS are either limited in terms of wavelength selectivity (e.g., lasers) or pulse energy (e.g., flash lamps). The pulse energy needed for adequate sensitivity for the present invention PAS methods depends upon the absorptivity of the sample to be analyzed and the efficiency of the PAS apparatus. The presently disclosed PAS methods may include use of a flash-lamp source suitable to provide a sufficient amount of energy for discrete wavelength applications. For example, the flash-lamp source may comprise a SQ xenon flash lamp available from Hamamatsu. Wavelength selectivity with minimal loss in pulse energy may be achieved with a flash-lamp source using narrow-band filters or reflectors for a limited number of wavelengths (as described in Autrey et al., Tunable UV Visible Photoacoustic Detection, *Anal. Chem. Acta*, (2001) which is incorporated herein by reference). Preferably, a large portion of the spectral output of the lamp is used to excite the affinity mass or recess in the sample array if there are not multiply component mixtures. E.g., for detecting various concentrations of a single analyte in the various affinity masses, the excitation source need not be narrow band.

For the disclosed PAS methods, when using variable pulse photoacoustic excitation sources, preferably sufficient energy densities are deposited in the sample to yield transient pressure changes of about $\geq 1$ mPa. Further, preferably, there is a ratio of transducer frequency ($s^{-1}$) to source pulse width(s) of about $\geq 5$. Preferably, the light source (or excitation source) has a pulse width of $<5$ $\mu s$ and more preferably, 2 $\mu s$ with pulse energy of greater than about 3 to about 30 $\mu J$. Pulse-laser sources may also be used to practice the methods of the present invention. The wave length of the light is preferably chosen based upon where the species of interest has the greatest absorbance and the affinity mass material has the least absorbance, as known to those persons skilled in the art.

A notch filter may be used to provide narrow-band light. Additionally, fiber optics and reflective mirrors may be utilized to direct a light beam from the light source to an affinity mass or recess. Because the intensity of the light source decreases with increasing distance from the source, however, optical mirrors mounted on the sample array may require a standardization method (as known to those persons skilled in the art) to normalize for changes in light intensity for each affinity mass or recess in the sample array. Preferably, optics to collimate the light focus on a fiber bundle, and to deliver the light beam to each sample affinity mass or recess in the sample array aid in the delivery of a constant path length for travel of the light beam. The light exiting such a fiber bundle is preferably shaped to provide an optimized energy density (as discussed above) for each affinity mass or recess in the sample array.

When using commercially available piezoelectric transducers for acoustic detectors, transient pressure changes in the order of 1 Pa can be detected with no electronic amplification of transducer signals. The use of low noise, high gain (e.g., 100–1000 gain) amplifiers available from Panametrics with the present methods permit the measure of mPa pressure changes with adequate signal averaging to reduce white noise. Analysis of equation (1) discussed above, showed that the photo-induced pressure change in the excitation volume (the sample volume to be analyzed) is equal to the product of the first two terms representing the density of the absorbed energy and the thermo-elastic properties of the solvent (i.e., term (1) absorbed incident light intensity per irradiated volume, term (2) expansivity, compressibility, heat capacity, and density of the solution in the recess or the material forming the affinity mass). For an analyte dissolved in water, each $\mu J$ per $\mu L^{-1}$ of absorbed energy should result in a pressure change of about ca. 135 mPa, and thus is detectable by a piezoelectric transducer available from Airmar or Stavely. The minimum pulse energy to reach the pulse threshold of a conventional piezoelectric transducer (i.e., about 1 mPa) can be estimated when the solution absorbance and the excitation volume are known.

A light beam (or other excitation beam) is directed to the affinity masses or recesses of the sample array in a manner that may depend upon the embodiment of the sample array being used (e.g., transmissive or reflective). For example, for an embodiment of a sample array similar to or the same as those illustrated in FIGS. 2, 3, and 6, a light path as shown in FIG. 9 may be used. With reference to FIG. 9, a light beam B is emitted from a light source (not shown) of the PAS system substantially perpendicularly to an affinity mass or sample recess retaining a sample S. The light beam B travels into and through the sample S and a support or substrate holding the sample, and is reflected back through the sample by the reflective coating or plate R. An acoustic wave AW created by absorption of energy by the sample S is then emitted from the sample and is detected by an acoustic detector D positioned below the sample S.

Figure 10A:
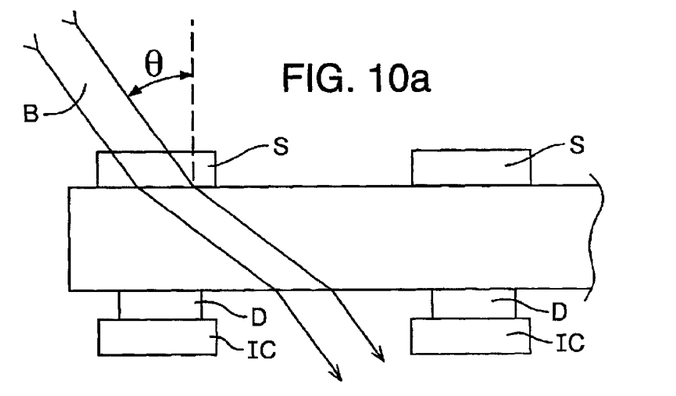
FIG. 10a illustrates a portion of an embodiment of a sample array comprising a refractive array.

Another example is illustrated in FIG. 10*a*, using a transmissive array. A light beam B is directed from a light source (not shown) at an angle $\theta$ into and refracts through sample S (retained in a recess and/or affinity mass) and through a support past an acoustic detector D. Angle $\theta$ may be less than the critical angle $\theta_c$ (known by those persons skilled in the art) to less than about 90 degrees and is preferably about an angle of about 45 degrees. An acoustic wave emitted from the irradiated sample S travels to the detector D as described above in relation to FIG. 9.

Figure 10B:
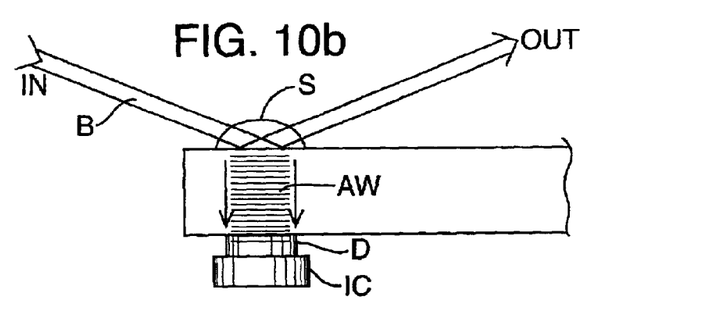
FIG. 10b illustrates a portion of an embodiment of a sample array comprising a reflective array.
Figure 11:
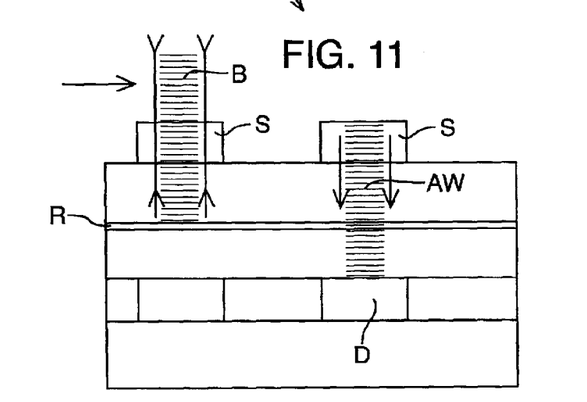
FIG. 11 is a side view of an embodiment of a sample array including separable affinity mass plates, reflective plates, and base plates.

With reference to FIG. 10*b*, in yet another example, a light beam B is directed from a light source (not shown) in a direction substantially parallel to an upper surface of the sample array, at an angle greater than the critical angle, $\theta_c$. The light beam B is reflected substantially (i.e., to produce total internal reflection "TIR") back through a sample S (comprising an affinity mass 40 or a recess). The acoustic waves AW created by absorption of energy by the sample S is then transmitted through the substrate or support to an acoustic detector D.

With reference to FIG. 12*b*, in yet another example, a light beam B may be directed from a light source (not shown) in a direction substantially perpendicular to an upper surface of the sample array. The light beam B is transmitted through an affinity mass 40 or a recess. An acoustic wave created by absorption of energy by the sample in the affinity mass 40 is then transmitted to the air above the affinity mass or recess and is preferably reflected by an acoustic reflector and to an acoustic detector 48 positioned above the affinity mass. In this embodiment, the reflector (not shown) transmits the excitation light waves and reflects the acoustic waves. Clearly, a PAS system used with a sample array may direct the light beam to a sample in a variety of manners (in addition to those outlined herein).

In embodiments of sample arrays having less than one acoustic detector per affinity mass or recess, to detect and characterize spectral peaks obtained from the transducers a statistical concept of a histogram is may be used. Specifically, in PAS an acoustic waveform is measured utilizing transducer output voltages as a function of time after pulsed excitation of the sample. The arrival time of an acoustic wave at the detector from a specific affinity mass or recess is dependent on the speed of sound in the sample array. Thus time-gating (as known to those skilled in the art) would provide locations from which affinity mass or recess provided the acoustic signal detected.

Whereas the invention has been described with reference to multiple embodiments of the apparatus and representative methods, it will be understood that the invention is not limited to those embodiments and representative methods. On the contrary, the invention is intended to encompass all modifications, alternatives, and equivalents as may be included within the spirit and scope of the invention as defined by the appended claims.

What is claimed is:

1. A sample array for PAS analysis comprising:
a body having an upper surface and a lower surface;
at least one affinity mass formed on the upper surface for holding a sample for PAS analysis;
a reflective coat connected to the lower surface for reflecting light beams that pass through the at least one affinity mass; and
an acoustic detector positioned to detect and capable of detecting acoustic signals that emanate from the sample in the at least one affinity mass.

2. The sample array of claim 1, wherein an acoustic detector is positioned adjacent each affinity mass to detect acoustic signals that emanate from the adjacent affinity mass.

3. The sample array of claim 1, wherein the acoustic detector is air-coupled to the sample array.

4. A PAS sample array comprising:

a substrate having an upper surface and a lower surface;

an array of affinity masses connected to the upper surface of the substrate;

a reflective plate connected to the lower surface of the substrate; and a base plate having an array of acoustic detectors connected thereto, wherein the base plate is positionable beneath the substrate such that each acoustic detector of the array connected to the base plate is positioned below an affinity mass, wherein each acoustic detector can receive acoustic signals emitted from an analyte retained in a respective affinity mass.

* * * * *

UNITED STATES PATENT AND TRADEMARK OFFICE
CERTIFICATE OF CORRECTION

| | | |
|---|---|---|
| PATENT NO. | : 6,870,626 B2 | Page 1 of 1 |
| APPLICATION NO. | : 10/001235 | |
| DATED | : March 22, 2005 | |
| INVENTOR(S) | : S. Thomas Autrey, Gerald J. Posakony and Chen Yu | |

It is certified that error appears in the above-identified patent and that said Letters Patent is hereby corrected as shown below:

In the Specification:

Column 4, line 44, "L" should read --µL--.

Signed and Sealed this

Thirteenth Day of March, 2007

JON W. DUDAS
*Director of the United States Patent and Trademark Office*